(12) United States Patent
Campton et al.

(10) Patent No.: US 10,101,248 B1
(45) Date of Patent: Oct. 16, 2018

(54) SOLUTION AND METHOD FOR ADHERING SUSPENSION COMPONENTS TO A SUBSTRATE

(71) Applicant: RareCyte, Inc., Seattle, WA (US)

(72) Inventors: Daniel Campton, Seattle, WA (US); Joshua Nordberg, Bainbridge Island, WA (US); Ronald Seubert, Sammamish, WA (US)

(73) Assignee: RareCyte, Inc., Seattle, WA (US)

( * ) Notice: Subject to any disclaimer, the term of this patent is extended or adjusted under 35 U.S.C. 154(b) by 0 days.

(21) Appl. No.: 15/787,185

(22) Filed: Oct. 18, 2017

Related U.S. Application Data

(63) Continuation-in-part of application No. 14/956,622, filed on Dec. 2, 2015.

(51) Int. Cl.
*G01N 1/30* (2006.01)
*G02B 21/34* (2006.01)

(52) U.S. Cl.
CPC .............. *G01N 1/30* (2013.01); *G02B 21/34* (2013.01); *G01N 2001/305* (2013.01)

(58) Field of Classification Search
None
See application file for complete search history.

(56) References Cited

U.S. PATENT DOCUMENTS

| | | | |
|---|---|---|---|
| 2,101,867 A * | 12/1937 | Miller | A61K 31/60 514/162 |
| 5,108,923 A * | 4/1992 | Benedict | A61L 27/38 435/174 |
| 5,256,571 A | 10/1993 | Hurley et al. | |
| 5,256,671 A * | 10/1993 | Ladduwahetty | C07D 453/02 514/214.03 |
| 7,803,624 B2 * | 9/2010 | Klautky | G01N 1/312 356/36 |
| 2002/0051849 A1 * | 5/2002 | Fox | C12N 5/0068 427/398.5 |
| 2005/0181353 A1 * | 8/2005 | Rao | A01N 1/02 435/1.1 |
| 2006/0024357 A1 * | 2/2006 | Carpenter | A61K 9/0024 424/445 |
| 2006/0088814 A1 * | 4/2006 | Hecht | A01N 1/02 435/2 |
| 2009/0275076 A1 | 11/2009 | Knesel et al. | |
| 2013/0022548 A1 * | 1/2013 | Bennett | A61K 49/12 424/9.3 |
| 2014/0227272 A1 * | 8/2014 | Kufer | A61K 31/10 424/135.1 |

* cited by examiner

*Primary Examiner* — Melvin C Mayes
*Assistant Examiner* — Colette B Nguyen
(74) *Attorney, Agent, or Firm* — Shay Glenn LLP

(57) ABSTRACT

This disclosure is directed to a method and an attachment solution for adhering a cytological or histological sample, such as buffy coat, to a substrate, such as a microscope slide. The attachment solution includes an attachment base, an anti-coagulant, and a nonsteroidal anti-inflammatory drug. The attachment base may be an alcohol, an acid, an oxidizer, an organohalogen, a ketone, or any combination thereof. Once a sample is obtained, the sample may be re-suspended in the attachment solution or the attachment solution may be added to the sample. The sample may then be dispensed onto an analysis platform as one or more droplets and cured.

4 Claims, 3 Drawing Sheets

SOLUTION AND METHOD FOR ADHERING SUSPENSION COMPONENTS TO A SUBSTRATE

CROSS-REFERENCE TO A RELATED APPLICATIONS

This application is a continuation-in-part of application Ser. No. 14/956,622, filed Dec. 2, 2015.

TECHNICAL FIELD

This disclosure relates generally to analyzing a suspension and, in particular, to a solution and method for adhering a component of a suspension to a substrate.

BACKGROUND

Current diagnostic methods and techniques rely on the interpretation of histological and cytological samples. It is an important aspect in these interpretations that the sample remains adhered to a substrate on which the samples are being analyzed and processed, such as a microscope slide. Valuable diagnostic information may then be obtained from the sample upon subsequent processing due to the adherence of the sample.

DETAILED DESCRIPTION

Figure 2:
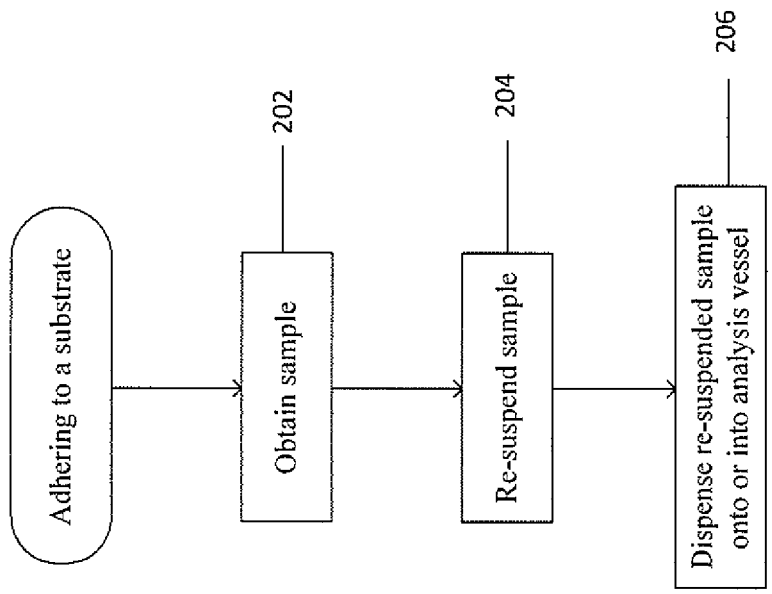
FIG. 2 shows a flowchart of an example method for adhering a sample to a substrate.

This disclosure is directed to a method and an attachment solution for adhering a cytological or histological sample to a substrate. The attachment solution includes an attachment base and a nonsteroidal anti-inflammatory drug. The attachment base may be an alcohol, an acid, an oxidizer, an organohalogen, a ketone, such as acetone, or any combination thereof, such as Carnoy's solution. The attachment solution may also include an anti-coagulant. Once a sample is obtained, the sample may be re-suspended in the attachment solution or the attachment solution may be added to the sample. The sample is dispensed onto an analysis platform as one or more droplets and cured. The sample may then be fixed, permeabilized, labeled, blocked, and washed. The sample may then be imaged and analyzed.

In the following description, the term "sample" is used to describe a specimen to be analyzed. The specimen may be a suspension, a portion of the suspension, or a component of the suspension. For example, when the suspension is anti-coagulated whole blood, the sample may be the anticoagulated whole blood (i.e. a suspension), the buffy coat (i.e. a portion of the suspension), or a circulating tumor cell (i.e. a component of the suspension).

Attachment Solution

The attachment solution may adhere a sample to a substrate. The sample can be a buffy coat of a blood sample and the substrate can be the surface of a microscope slide. The attachment solution includes an attachment base and a nonsteroidal anti-inflammatory drug. The attachment solution may also include water. A buffer may also be included or a buffered solution may be used in place of or in addition to the water. A buffer or a buffer of the buffered solution may include, but is not limited to, ACES, ADA, AMP, AMPD, AMPSO, BES, Bicine, BIS-TRIS, BIS-TRIS propane, CABS, CAPS, CAPSO, CHES, DIPSO, EDTA, HEPPS (EPPS), Gly-Gly, HEPBS, HEPES, MES, MOPS, MOPSO, PIPES, POPSO, potassium phosphate, sodium phosphate (monobasic and/or dibasic), TAPS, TAPSO, TES, Tricine, tris, Trizma®, and combinations thereof. The pH of the buffer or buffer solution may range from 5 to 12.

It should be noted that in a first embodiment, the attachment solution includes a salt, such as that in a saline solution, where the attachment solution remains hypotonic relative to the sample, as an isotonic or hypertonic attachment solution may cause the sample to crack while drying or curing. Alternatively, the attachment solution does not include a salt, such as that included in a saline solution, as the salt may cause the sample to crack while drying or curing.

The attachment base may include an alcohol, such as ethanol, methanol, propanol, isopropanol, butanol, and an acid, an oxidizer, an organohalogen, a ketone, such as acetone, or any combination thereof, such as Carnoy's solution. The attachment base may be capable of fixing sample components, such as cells, without cross-linking other sample components, such as proteins. Preventing cross-linking of the other sample components, such as proteins, may avoid an additional processing step, such as antigen retrieval. In other words, fixing sample components to a substrate with the attachment base eliminates the process of antigen retrieval. The attachment base may also have a fast (i.e. less than one hour) cure time. The attachment base may have a final concentration, such as when the attachment solution and the sample have been mixed, of 60-70% by volume, and more specifically 63-68% by volume. Having a concentration of the attachment base outside the desired range may affect the sample or a portion thereof, such as by lysis, clumping, inability to adhere to the substrate, or the like. The final concentration of the attachment base may be determined by a measured property of the sample to be adhered including, but not limited to, sample volume, packed cell volume, hematocrit level, blood type, sample type (i.e. blood, urine, buffy coat, single cell, etc.), or the like.

The nonsteroidal anti-inflammatory drug may be, but is not limited to, acetylsalicylic acid, celecoxib (Celebrex), diclofenac (Voltaren), diflunisal (Dolobid), etodolac (Lodine), ibuprofen (Motrin), indomethacin (Indocin), ketoprofen (Orudis), ketorolac (Toradol), nabumetone (Relafen), naproxen (Aleve, Naprosyn), oxaprozin (Daypro), piroxicam (Feldene), salsalate (Amigesic), sulindac (Clinoril), tolmetin (Tolectin), or the like. The nonsteroidal anti-inflammatory drug may act as an antithrombotic (i.e. reducing blood clotting, such as by reducing the blood clotting function of various blood components). The nonsteroidal anti-inflammatory drug may have a final concentration of 100-1000 ug/mL.

The attachment solution may also include an anti-coagulant which may be, but is not limited to, heparin, heparin sodium, heparin/dextrose, ethylene-diamine-tetra-acetic acid, dalteparin sodium, argatroban, bivalirudin, lepirudin, or the like. The anti-coagulant prevents coagulation (i.e. clumping, clotting or solidification) of the sample. The anti-coagulant may have a final concentration of 10-1000 ug/mL.

The attachment solution may also include a biological polymer to increase the adhesion between the sample and the substrate. The biological polymer may include, but is not limited to, biomimetic adhesive polymers (such as polyphenolic protein from marine life; 3,4-dihydroxyphenylalanine), fibrin glue, gelatin-resorcinol-formaldehyde, poly-L-lysine, poly-D-lysine, or the like.

Method of Making Attachment Solution

The following are example reagents used to make attachment solutions:
1. Heparin 2000 μg/mL: Prepared by dissolving 20 mg of heparin sodium salt (Sigma H3393) in 10 mL of water
2. BD Cell-Tak: BD Cell-Tak® Cell and Tissue Adhesive (BD 354241)—approximately 1500 μg/mL stock concentration
3. Cell-Tak Buffer 5×: Prepared by dissolving 21 g sodium bicarbonate (NaHCO$_3$) into 500 mL of water
4. Cell-Tak Buffer 1×: Prepared by dissolving 4.2 g sodium bicarbonate (NaHCO$_3$) into 500 mL of water and adding 2.5 mL 1M hydrochloric acid (HCl)
5. Sigma Aldrich 494437: Methanol (about 99.93% by volume)

Figure 1:
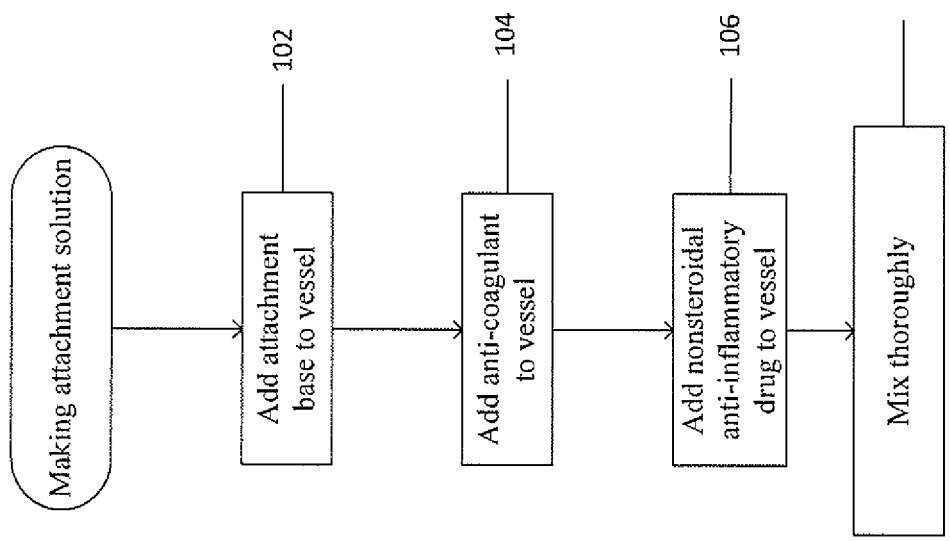
FIG. 1 shows a flowchart of an example method for making an example attachment solution.

The following are example formulations for attachment solutions, as seen in FIG. 1:
1. 70% Methanol by volume, 100 ug/mL Heparin, 300 ug/mL of acetylsalicylic acid, 50 ug/mL Cell-Take:
    A. Mix 350 uL of Cell-Take with 650 uL of Cell-Tak Buffer 1×
    B. Mix thoroughly
    C. Add 1.5 mL of water
    D. Add 500 uL of Heparin 2000 ug/mL
    E. Add 7.0 mL of Methanol
    F. Add 3000 ug of acetylsalicylic acid
    G. Mix thoroughly
2. 60% Methanol by volume, 300 ug/mL of acetylsalicylic acid:
    A. Add 6000 uL of methanol to 4000 uL of water
    B. Add 3000 ug of acetylsalicylic acid
    C. Mix thoroughly Method of Using Attachment Solution FIG. 2 shows an example method for adhering a sample to a substrate. In block 202, a sample is obtained. To obtain the sample, the sample may be withdrawn directly from a subject or the sample may undergo enrichment and/or isolation from the suspension. The sample may be enriched by any appropriate enrichment process including, but not limited to, sequential density fractionation, magnetic-activated cell sorting, fluorescence-activated cell sorting, differential lysis, depletion filters, or the like. Sequential density fractionation is a process by which a suspension is divided into fractions or a fraction of a suspension is divided into sub-fractions by a step-wise or sequential process, such that each step or sequence results in the collection or separation of a different fraction or sub-fraction from the preceding and successive steps or sequences. The sample may be obtained from other suspension components by selecting the sample with a device for picking, such as a cell picker, a pipet, a syringe, or the like.

Figure 3B:
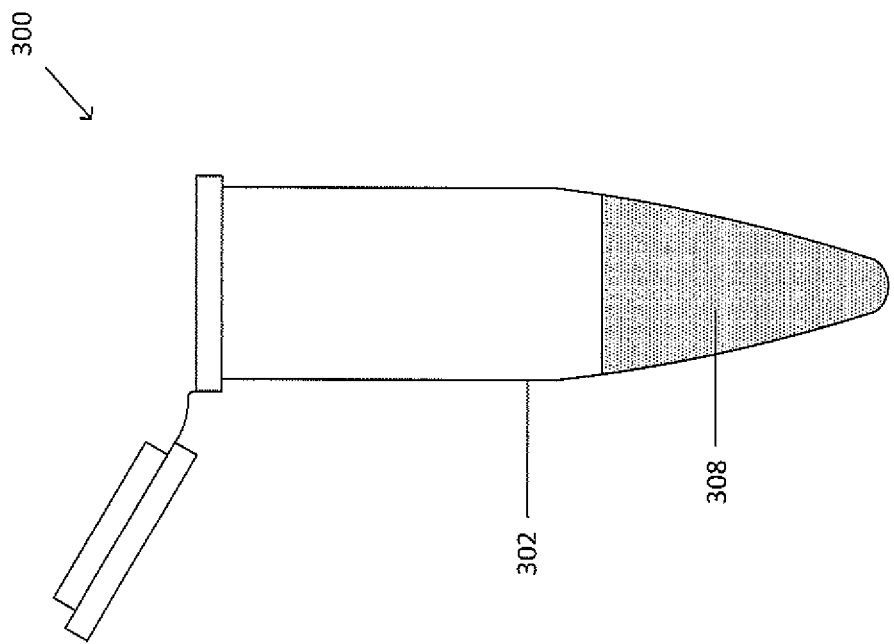
FIG. 3B shows the example sample mixing with the attach solution to form a re-suspended cytological sample.
Figure 3A:
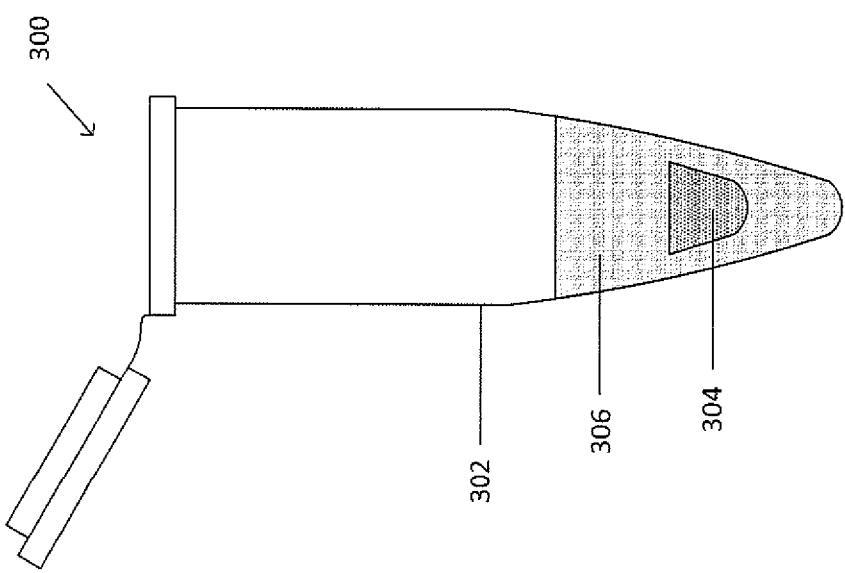
FIG. 3A shows an example sample having been re-suspended in an example attachment solution.
Figure 3C:
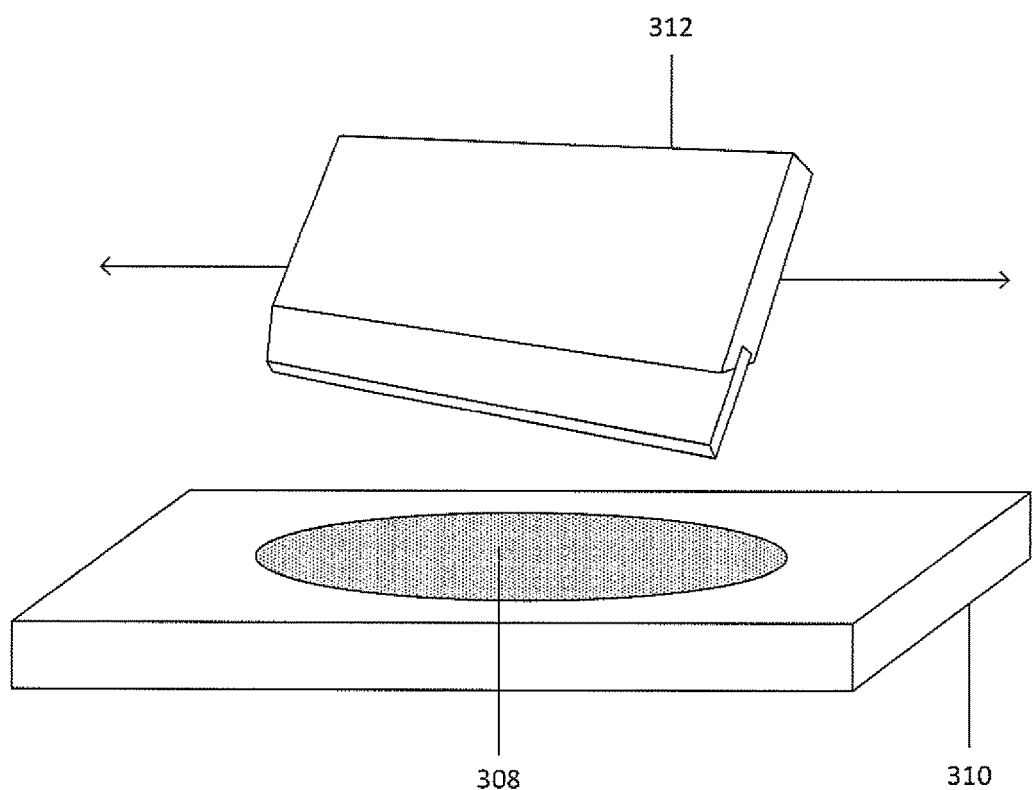
FIG. 3C shows the re-suspended sample being deposited on an example analysis platform.
Figure 3D:
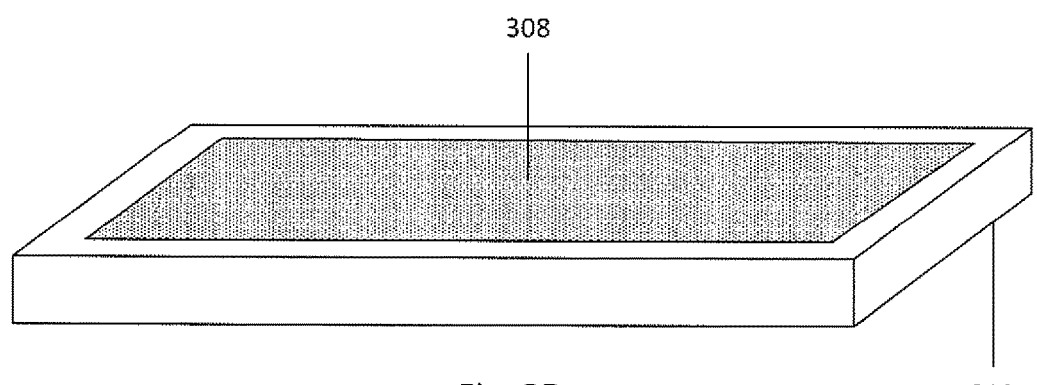
FIG. 3D shows the re-suspended sample having been spread on and adhered to the analysis platform.

Referring back to FIG. 2, in block 204, the sample 304 is re-suspended in an attachment solution 306 in a vessel 302, as shown in FIG. 3A. Alternatively, the attachment solution may be added to or mixed with the sample. In block 206, the re-suspended sample 308, which includes at least a portion of the attachment solution, as shown in FIG. 3B, is dispensed onto or into an analysis platform 310 by a dispenser, such as a pipet or repeating pipet, and spread across the analysis platform. In FIG. 3C, the sample 308 is spread across the analysis platform 310 by a spreader 312, such as a squeegee, a pipet tip, a blade, a two-piece spreader including a blade and a base. Alternatively, the sample 308 may be spread across the analysis platform 310 by centrifuging, wetting, or nutating the analysis platform 310. The re-suspended sample 308 is cured, as shown in FIG. 3D, to adhere the re-suspended sample 308 to the analysis platform 310. Alternatively, the re-suspended sample 308 may be dispensed onto the analysis platform 310 and cured without being spread across the analysis platform 310. Curing may occur in air, such as at room temperature; in an environmentally-controlled chamber, such as at 37° C.; or the like. Furthermore, the sample may undergo an additional fixation step, such as in formalin or any appropriate fixative, after the curing step has been completed.

The attachment solution may be compatible with any appropriate analysis method or technique, though more specifically extracellular and intracellular analysis including immunofluorescent labeling and imaging; intracellular protein labeling; chromogenic staining; molecular analysis; genomic analysis or nucleic acid analysis, including, but not limited to, genomic sequencing, DNA arrays, expression arrays, protein arrays, and DNA hybridization arrays; in situ hybridization ("ISH"—a tool for analyzing DNA and/or RNA, such as gene copy number changes); polymerase chain reaction ("PCR"); reverse transcription PCR; or branched DNA ("bDNA"—a tool for analyzing DNA and/or RNA, such as mRNA expression levels) analysis. Some of the intracellular proteins which may be labeled include, but are not limited to, cytokeratin ("CK"), actin, Arp2/3, coronin, dystrophin, FtsZ, myosin, spectrin, tubulin, collagen, cathepsin D, ALDH, PBGD, Akt1, Akt2, c-myc, caspases, survivin, p27$^{kip}$, FOXC2, BRAF, Phospho-Akt1 and 2, Phospho-Erk1/2, Erk1/2, P38 MAPK, Vimentin, ER, PgR, PI3K, pFAK, KRAS, ALKH1, Twist1, Snail1, ZEB1, Fibronectin, Slug, Ki-67, M30, MAGEA3, phosphorylated receptor kinases, modified histones, chromatin-associated proteins, and MAGE.

The analysis platform 310 may be a microscope slide, a positively charged microscope slide, a coated microscope slide, a porous slide, a micro-well slide, a well plate, a coverslip, a cell microarray, or the like. The analysis platform 310 may be any appropriate material, including, but not limited to, glass, plastic, ceramic, metal, or the like.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents:

We claim:

1. A solution consisting essentially of:
   an alcohol having a final concentration of 60-70% by volume;
   acetylsalicyclic acid having a final concentration of 100-1000 ug/mL; and
   water,
   wherein the final concentrations are the concentrations of the respective components when mixed with a sample.

2. The solution of claim 1, wherein the alcohol is methanol.

3. The solution of claim 1, further comprising a buffer.

4. The solution of claim 1, further comprising a salt, wherein the solution is hypotonic relative to the sample.

* * * * *